(12) United States Patent
Ambhaikar et al.

(10) Patent No.: US 8,404,865 B2
(45) Date of Patent: *Mar. 26, 2013

(54) PROCESS FOR PREPARING AZABICYCLIC COMPOUNDS

(75) Inventors: Narendra Bhalchandra Ambhaikar, Hyderabad (IN); Brian Richard Bear, Oceanside, CA (US); Lev T. D. Fanning, San Marcos, CA (US); Robert Hughes, San Diego, CA (US); Benjamin Littler, Carlsbad, CA (US)

(73) Assignee: Vertex Pharmaceuticals, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/884,925

(22) Filed: Sep. 17, 2010

(65) Prior Publication Data

US 2011/0065928 A1 Mar. 17, 2011

Related U.S. Application Data

(60) Provisional application No. 61/243,477, filed on Sep. 17, 2009.

(51) Int. Cl.
*C07D 487/08* (2006.01)
(52) U.S. Cl. ...................................... 548/453
(58) Field of Classification Search .................. None
See application file for complete search history.

(56) References Cited

U.S. PATENT DOCUMENTS

| 7,495,103 | B2 | 2/2009 | Hadida-Ruah et al. |
| 2010/0113508 | A1 | 5/2010 | Binch et al. |
| 2010/0130547 | A1 | 5/2010 | Zhang et al. |

FOREIGN PATENT DOCUMENTS

WO   WO2011050215   * 10/2009

OTHER PUBLICATIONS

Fraser, R.R., et al., "Synthesis of 7-azabicyclo[2.2.1]heptane, exo-2-chloro-7-azabicyclo[2.2.1]heptane and derivatives," Canadian Journal of Chemistry, 1970, vol. 48, pp. 2065-2074, XP002613119.
International Search Report for PCT/US2010/049306 dated Dec. 7, 2010.
Chen, Zhengming, et al., "Chemistry of 7-Azabicyclo[2.2.1]hepta-2,5-dienes, 7-Azabicyclo[2.2.1]hept-2-enes, and 7-Azabicyclo[2.2.1]heptanes," Chemical Reviews, 1996, vol. 96, No. 3, pp. 1179-1193.
Cheng, Jie, et al., "Synthesis of N-Heteroaryl-7-azabicyclo[2.2.1]heptane Derivatives via Palladium-Bisimidazol-2-ylidene Complex Catalyzed Amination Reactions," Organic Letters, 2001, vol. 3, No. 9, pp. 1371-1374.
Nelsen, Stephen F., et al., "The Nitrogen Inversion Barrier of 7-Methyl-7-azabicyclo[2.2.1]heptane and the Bicyclic Effect," JACS, 1989, vol. 111, No. 5, pp. 1776-1781.
Olivo, Horacio F., et al., "Microbial C-hydroxylation and B-4-O-methylglucosidation of methyl-benzamide 7-azanorbornane ethers with *Beauveria bassiana*," Journal of Molecular Catalysis B: Enzymatic 21, 2003, pp. 97-105.
Otani, Yuko, et al., "An Evaluation of Amide Group Planarity in 7-Azabicyclo[2.2.1]heptane Amides. Low Amide Bond Rotation Barrier in Solution," JACS, 2003, vol. 125, No. 49, pp. 15191-15199.

* cited by examiner

*Primary Examiner* — Sun Jae Loewe
(74) *Attorney, Agent, or Firm* — Honigman Miller Schwartz and Cohn LLP; Christopher C. Forbes; Jonathan P. O'Brien

(57) ABSTRACT

The present invention relates to a process for preparing azabicyclic compounds that are useful intermediates for synthesizing pharmaceutical compounds or salts thereof.

20 Claims, No Drawings

PROCESS FOR PREPARING AZABICYCLIC COMPOUNDS

CROSS-REFERENCE TO RELATED APPLICATIONS

This application claims priority to provisional application U.S. Ser. No. 61/243,477 filed on Sep. 17, 2009. The entire contents of the aforementioned application are incorporated herein.

TECHNICAL FIELD OF THE INVENTION

The present invention relates to a process for preparing azabicyclic compounds that are useful in the synthesis of pharmaceutical compounds and salts thereof.

BACKGROUND OF THE INVENTION 7-azabicyclo[2.2.1]heptanes are useful intermediates in the synthesis of pharmaceutical compounds and salts thereof. For example, see U.S. Pat. Nos. 6,117,889 and 6,060,473, each of which is hereby incorporated by reference in its entirety.

SUMMARY OF THE INVENTION

What is disclosed herein is a process for preparing azabicyclic compounds that are useful intermediates for preparing pharmaceutical compounds and salts thereof.

DETAILED DESCRIPTION OF THE INVENTION

Definitions

Compounds and processes disclosed herein include those described generally above, and are further illustrated by the classes, subclasses, and species disclosed herein. As used herein, the following definitions shall apply unless otherwise indicated.

The term "modulating" as used herein means increasing or decreasing by a measurable amount.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent.

Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, particularly compounds that contain deuterium atoms, may exhibit modified metabolic properties.

In one aspect, the invention includes a process for preparing Compound 7,

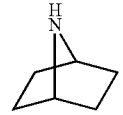

7 or a pharmaceutically acceptable salt thereof, comprising contacting trans-4-aminocyclohexanol with Boc anhydride to produce a compound of formula A

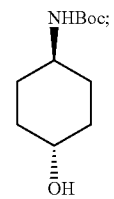

A contacting a compound of formula A with methanesulfonic acid to produce a compound of formula B

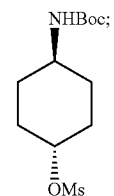

B contacting a compound of formula B with trifluoroacetic acid to produce a compound of formula C

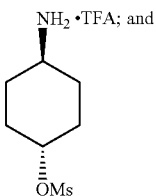

contacting a compound of formula C with hydroxide to produce a compound of formula 7.

In some embodiments, the invention includes a method of producing a compound of formula 7a,

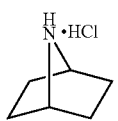

comprising contacting a compound of formula 8 with hydrochloric acid.

In one embodiment, trans-4-aminocyclohexanol is contacted with Boc anhydride in the presence of a solvent and optionally in the presence of a base.

In another embodiment, the solvent comprises water, dichloromethane, THF, 2-methyltetrahydrofuran, ethanol, methanol, isopropanol, DMF, DMSO, or combinations thereof.

In one embodiment, the solvent is a mixture.

In a further embodiment, the solvent is a mixture comprising water and dichloromethane.

In one embodiment, a base is present and the base comprises sodium bicarbonate, potassium bicarbonate, sodium carbonate, potassium carbonate, or combinations thereof.

In another embodiment, a compound of formula A is contacted with methanesulfonic acid in the presence of a solvent and optionally in the presence of a base.

In one embodiment, the solvent comprises tetrahydrofuran.

In another embodiment, a base is present and the base comprises a tertiary amine base.

In a further embodiment, the base is triethylamine.

In one embodiment, the compound of formula B is contacted with trifluoroacetic acid in the presence of a solvent.

In a further embodiment, the solvent is dichloromethane.

In another embodiment, the compound of formula B is contacted with trifluoroacetic acid under neat conditions.

In one embodiment, the compound of formula C is contacted with hydroxide in the presence of a solvent.

In a further embodiment, the hydroxide is present as sodium hydroxide or potassium hydroxide and the solvent comprises water.

In one embodiment, the process further comprises distillation of the reaction mixture and recovery of a compound of formula 7 in a pure form.

In one embodiment, the process further comprises recrystallizing Compound 7a from acetonitrile.

In another embodiment, the process further comprises recrystallizing Compound 7a from a mixture of methanol and 2-methyltetrahydrofuran.

In one embodiment, the ratio of methanol to 2-methyltetrahydrofuran is about 1:1.

Formulations

The pharmaceutically acceptable compositions that can include the azabicyclic compound of the present invention or pharmaceuticals synthesized therefrom may additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds of the invention may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions can be administered to humans and other animals orally, rectally, parenterally, intracistemally, intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

The amount of additional therapeutic agent present in the compositions will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Preparation of Azabicyclic Compounds

Scheme 1: Preparation of 7-azabicyclo[2.2.1]heptane hydrochloride (7a).

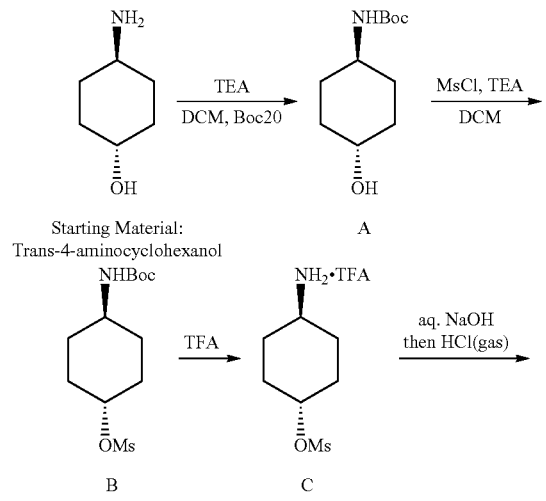

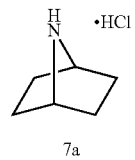

7a

Preparation of trans-4-(tert-butoxycarbonylamino)cyclohexanol (A), method 1. Sodium carbonate (920.2 g, 8.682 mol, 2 eq) was added to a reaction vessel followed by an addition of water (3.000 L, 6 vol) and stirring. Dichloromethane (DCM, 4.000 L, 4 vol) was added followed by trans-4-aminocyclohexanol (500.0 g, 4.341 mol) to generate a biphasic reaction mixture that was vigorously stirred at room temperature. A solution of $Boc_2O$ (947.4 g, 997.3 mL, 4.341 mol, 1 eq) in DCM (2 vol) was then rapidly added dropwise to the vessel, and the resulting reaction mixture was stirred at room temperature overnight. The reaction mixture was then filtered and the filter cake was washed with water (2×8 vol). The product was suction-dried until it was a compact cake. The cake was then dried in a vacuum oven at 35° C. for 24 h giving 830 g of trans-4-(tert-butoxycarbonylamino)cyclohexanol (A) as a crystalline solid.

Preparation of trans-4-(tert-butoxycarbonylamino)cyclohexanol (A), method 2. Two 50 L three-neck round bottom flasks were each equipped with a mechanical stirrer and thermocouple. The flasks were placed in a cooling tub, and then each flask was charged with water (8.87 L) and trans-4-aminocyclohexanol (1479 g). After about 10 to 30 minutes, the trans-4-aminocyclohexanol had dissolved, and potassium carbonate (1774.6 g) was added to each flask. After about 10 to 20 minutes, the potassium carbonate had dissolved, and DCM (2.96 L) was charged to each flask. Boc anhydride (3082.6 g) in DCM (1479 mL) was then added to each flask at such a rate as to maintain the temperature at 20 to 30° C. An ice/water bath was used to control the exotherm and to accelerate the addition, which took approximately 1 to 2 hours. A suspension formed during the addition, and the reaction mixtures were allowed to warm to room temperature and stirred overnight, until the reaction was complete based on the disappearance of the Boc anhydride. Heptane (6 L) was then charged to each flask, and the mixtures were cooled to approximately 0 to 5° C. Solids were collected from each flask by filtration using the same filter. The combined solids were washed with heptane (6 L) followed by water (8 L). The solids were charged to an appropriately sized crock equipped with a mechanical stirrer. Water (12 L) and heptane (6 L) were added, and the resulting suspension was mechanically stirred for 30 to 60 minutes. The solids were collected by filtration and then washed on a filter with water (8 L) and heptane (8 L), air-dried on a filter for three days, and then dried under vacuum at 30 to 35° C. to a constant weight to provide the product as a white solid.

Preparation of trans-4-(tert-butoxycarbonylamino)cyclohexylmethanesulfonate (B), method 1. A 12 L flask was equipped with a nitrogen flow and a mechanical stirrer. Trans-4-(tert-butoxycarbonylamino)cyclohexanol (750 g, 3.484 mol) was introduced, followed by tetrahydrofuran (THF, 6.000 L, 8 vol), and the mixture was stirred. Triethylamine (370.2 g, 509.9 mL, 3.658 mol, 1.05 eq) was added and the mixture was cooled to 0° C. Methanesulfonyl chloride (419.0 g, 283.1 mL, 3.658 mol, 1.05 eq) was carefully added dropwise, keeping the temperature of the mixture below 5° C. After the addition, the mixture was stirred at 0° C. for 3 h, and then gradually warmed to room temperature (17° C.) and stirred overnight (about 15 h). The mixture was quenched with water (6 vol) and stirred for 15 min. Ethyl acetate (EtOAc, 9.000 L, 12 vol) was added and the stirring was continued for 15 min. The stirring was stopped and the mixture was allowed to stand for 10 min, and the aqueous phase was removed. 1 N HCl (6 vol, 4.5 L) was added and stirring was continued for 15 min. The stirring stopped and the aqueous phase was removed. 10% w/v NaHCO$_3$ (4.5 L, 6 vol) was added and the mixture stirred for 10 min. Stirring was stopped and the aqueous phase was removed. Water (6 vol, 4.5 L) was added and the mixture was stirred for 10 min. The aqueous layer was removed, and the organic layer was polish filtered and concentrated to 4 vol. Heptane (5.5 vol, 4 L) was added and the mixture was concentrated again to dryness resulting in 988 g of trans-4-(tert-butoxycarbonylamino)cyclohexylmethanesulfonate.

Preparation of trans-4-(tert-butoxycarbonylamino)cyclohexylmethanesulfonate (B), method 2. A three-neck round bottom flask equipped with a mechanical stirrer, addition funnel, nitrogen inlet, thermocouple and drying tube was placed into a cooling tub. Trans-4-(tert-butoxycarbonylamino)cyclohexanol (2599 g, 12.07 mol, 1.0 eq), tetrahydrofuran (THF) (20.8 L), and triethylamine (1466 g, 14.49 mol, 1.2 eq) were added to the flask. The mixture was cooled with an ice water bath and stirred. Methanesulfonyl chloride (1466 g, 12.80 mol, 1.06 eq) was added dropwise by addition funnel over 1 hour. Once the addition was complete, the cooling bath was removed, and the reaction mixture was stirred until TLC indicated the starting material was consumed (about 30 minutes). The reaction mixture was then quenched with an aqueous solution of hydrochloric acid (223 mL of HCl in 6.7 L of water) and EtOAc (10.4 L). The mixture was stirred for approximately 10 to 20 minutes at ambient temperature and then was transferred to a separatory funnel. The layers were separated, and the aqueous layer discarded. The organic layer was washed with water (2×4.5 L), aqueous saturated sodium bicarbonate solution (1×4.5 L), and dried over anhydrous magnesium sulfate with stirring for 5 to 10 minutes. The mixture was filtered and the filter cake was washed with EtOAc (2×600 mL). The combined washes and filtrate were concentrated under reduced pressure at 40° C., leaving a white solid. The solid was taken up in heptane (3 L) and cooled in an ice/methanol cooling tub. More heptane (5 L) was added, and the mixture was stirred at 0 to 5° C. for not less than 1 hour. The solids were then collected by filtration, washed with cold heptane (0 to 5° C., 2×1.3 L), and dried under vacuum at 40° C. to a constant weight to provide the captioned compound.

Note: A jacketed reactor may be used instead of a round bottom flask with a cooling tub and ice bath.

Preparation of trans-4-aminocyclohexylmethanesulfonate (C), method 1. Trans-4-(tert-butoxycarbonylamino)cyclohexylmethanesulfonate (985 g, 3.357 mol) was introduced into a 3-neck 12 L flask equipped with a stirrer under a nitrogen atmosphere and open vent. DCM (1.970 L, 2 vol) was added at room temperature, and stirring was commenced. Trifluoroacetic acid (TFA) (2.844 kg, 1.922 L, 24.94 mol, 2 vol) was slowly added to the mixture in two batches of 1 L each. After the first addition, the mixture was stirred for 30 min followed by a second addition. The mixture was stirred overnight (15 h) at room temperature resulting in a clear solution. 2-methyltetrahydrofuran (4 vol) was then added to the reaction mixture, which was stirred for 1 h. The mixture was then carefully filtered in a fume hood and suction dried to generate 1100 g of TFA salt of trans-4-aminocyclohexylmethanesulfonate with excess TFA.

Preparation of trans-4-aminocyclohexylmethanesulfonate (C), method 2. A 50 L three-neck round bottom flask was equipped with a mechanical stirrer, addition funnel and thermocouple and was placed into a cooling tub. To the flask was added trans-4-(tert-butoxycarbonylamino)cyclohexylmethanesulfonate (3474 g, 1.0 eq) and DCM (5.9 L) to the flask. The resulting suspension was stirred for 5 to 10 minutes at ambient temperature, and then trifluoroacetic acid (TFA, 5.9 L) was added via addition funnel slowly over 2.5 hours to control the resulting exotherm and rate of gas evolution. The reaction mixture was stirred at room temperature overnight and then cooled to 15° C. to 20° C. using an ice water bath. 2-Methyl tetrahydrofuran (2-MeTHF, 11.8 L) was then added via the addition funnel at a rate to maintain the internal temperature below 25° C. (approximately 1.5 hours). The addition of the first 4-5 L of 2-MeTHF was exothermic. The resulting suspension was stirred for 1 hour. The solids were collected by filtration and then washed with 2-MeTHF (2×2.2 L) and then dried under vacuum at ambient temperature to a constant weight to provide the captioned compound as a white solid.

Preparation of 7-azabicyclo[2.2.1]heptane hydrochloride (7a), method 1. The TFA salt of trans-4-aminocyclohexylmethanesulfonate (200 g, 650.9 mmol) was introduced into a 3-necked flask followed by the addition of water (2.200 L, 11 vol). NaOH (78.11 g, 1.953 mol, 3 eq) was slowly added, keeping the temperature of the reaction mixture below 25° C. and the mixture was stirred overnight. DCM (1.4 L, 7 vol) was then added and the mixture stirred, and the organic layer was separated. The aqueous layer was then extracted a second time with DCM (1.4 L, 7 vol), and the DCM layers were combined. HCl (108.5 mL, 12M, 1.3020 mol, 2 eq) was then added, the mixture was stirred for 30 min and then concentrated on a rotary evaporator to dryness. Acetonitrile (10 vol) was added and the mixture concentrated. This was repeated 3 times until all trace water was azeotropically removed, to provide 7-azabicyclo[2.2.1]heptane hydrochloride. The crude product was recrystallized from acetonitrile (10 vol) to provide 7-azabicyclo[2.2.1]heptane hydrochloride 7a as a colorless crystalline solid. $^1$HNMR (DMSO-d$^6$) ppm 8.02-8.04 (d); 7.23-7.31 (m); 4.59 (s); 3.31 (s); 2.51-3.3 (m); 1.63-1.75 (m); 1.45-1.62 (m).

As a note, instead of adding DCM for extraction, the crude product can also be distilled at about 95° C. to 97° C. and further recrystallized.

Preparation of 7-azabicyclo[2.2.1]heptane hydrochloride (7a), method 2. A 50 L three neck round bottom flask equipped with a mechanical stirrer, addition funnel and thermocouple and was placed into a heating mantle. Trans-4-aminocyclohexylmethanesulfonate trifluoroacetate in (3000 g, 1 eq) and water (30 L) were added to the flask. The mixture was stirred, as 50% NaOH (2343 g, 29.29 mol, 3 eq) was added by an addition funnel at such a rate as to maintain the temperature below 25° C. because the addition was mildly exothermic. Upon completion of the NaOH addition, the reaction mixture was stirred overnight at room temperature. The product was recovered by fractional distillation at reflux temperature, (approximately 100° C.) with a head temperature of 95° C. to 98° C. The pH of each fraction was adjusted to 2 by adding HCl, and concentrated under reduced pressure at 55° C. to leave a thick paste. Acetonitrile (ACN 1.5 L) was added and the resulting suspension was stirred for 30 minutes and then cooled to 0° C. to 5° C. for 1 hour. The solids were collected by filtration, washed with cold (0 to 5° C.) ACN (2×600 mL), and dried under vacuum at 50° C. to a constant weight.

A 22 L three-neck round bottom flask was equipped with a mechanical stirrer, thermocouple, and condenser and placed into a heating mantle. The collected solids (2382 g), methanol (4.7 L) and 2-MeTHF (4.7 L) were added to the flask. The resulting suspension was stirred and heated to reflux (approximately 65° C.). The reaction flask was transferred to a cooling tub, and the mixture was stirred. 2-MeTHF (4.7 L) was then added via addition funnel over 30 minutes. The resulting suspension was cooled to 0 to 5° C. and stirred at this temperature for 30 minutes. The solids were collected by filtration, washed with cold (0 to 5° C.) 2-MeTHF (2×600 mL), and then dried under vacuum at 55° C. to a constant weight.

A 12 L three-neck round bottom flask equipped with a mechanical stirrer, thermocouple, nitrogen inlet and condenser was placed into a heating mantle. The crude product (2079 g) and ACN (6.2 L) were added to the flask. The resulting suspension was stirred and heated to reflux (approximately 82° C.) for 30 minutes. The flask was transferred to a cooling tub and the suspension was slowly cooled to 0 to 5° C. and maintained at this temperature for 1 hour. The solids were collected by filtration, washed with cold (0 to 5° C.) ACN (3×600 mL), and dried under vacuum at 55° C. to a constant weight affording to provide the captioned product.

What is claimed is:

1. A process for preparing Compound 7,

7 or a pharmaceutically acceptable salt thereof, comprising contacting trans-4-aminocyclohexanol with Boc anhydride to produce Compound A

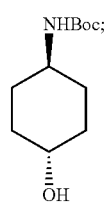

A contacting Compound A with methanesulfonyl chloride to produce Compound B

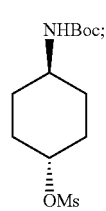

B contacting Compound B with trifluoroacetic acid to produce Compound C

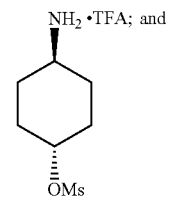

C contacting Compound C with hydroxide to produce Compound 7.

2. The process of claim 1, further comprising a process for producing Compound 7a,

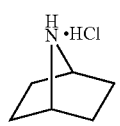

7a comprising contacting compound 7 with HCl.

3. The process of claim 1, wherein trans-4-aminocyclohexanol is contacted with Boc anhydride in the presence of a solvent and optionally in the presence of a base.

4. The process of claim 3, wherein the solvent comprises water, dichloromethane, THF, 2-methyltetrahydrofuran, ethanol, methanol, isopropanol, DMF, DMSO, or combinations thereof.

5. The process of claim 4, wherein the solvent is a mixture.

6. The process of claim 5, wherein the solvent is a mixture comprising water and dichloromethane.

7. The process of claim 3, wherein a base is present and the base comprises sodium bicarbonate, potassium bicarbonate, sodium carbonate, potassium carbonate, or combinations thereof.

8. The process of claim 1, wherein Compound A is contacted with methanesulfonyl chloride in the presence of a solvent and optionally in the presence of a base.

9. The process of claim 8, wherein the solvent comprises tetrahydrofuran.

10. The process of claim 8, wherein a base is present and the base comprises a tertiary amine base.

11. The process of claim 10, wherein the base is triethylamine.

12. The process of claim 1, wherein Compound B is contacted with trifluoroacetic acid in the presence of a solvent.

13. The process of claim 12, wherein the solvent is dichloromethane.

14. The process of claim 1, wherein Compound C is contacted with hydroxide in the presence of a solvent.

15. The process of claim 14, wherein the hydroxide is present as sodium hydroxide or potassium hydroxide and the solvent comprises water.

16. The process of claim 1, further comprising distillation of the reaction mixture and recovery of Compound 7 in a pure form.

17. The process of claim 2, further comprising recrystallizing Compound 7 a from acetonitrile.

18. The process of claim 2, further comprising recrystallizing Compound 7 a from a mixture of methanol and 2-methyltetrahydrofuran.

19. The process of claim 18, wherein the ratio of methanol to 2-methyltetrahydrofuran is about 1:1.

20. A process for preparing Compound 7a,

7a or a pharmaceutically acceptable salt thereof, comprising contacting trans-4-aminocyclohexanol with Boc anhydride to produce Compound A

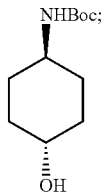
A contacting Compound A with methanesulfonyl chloride to produce Compound B

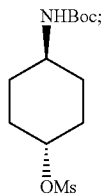
B contacting Compound B with trifluoroacetic acid to produce Compound C

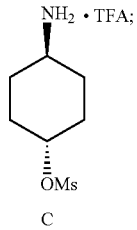
C contacting Compound C with hydroxide to produce Compound 7

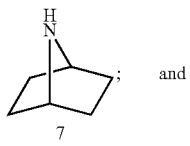; and
7 contacting Compound 7 with HCl to produce Compound 7a.

* * * * *

UNITED STATES PATENT AND TRADEMARK OFFICE
CERTIFICATE OF CORRECTION

PATENT NO. : 8,404,865 B2  
APPLICATION NO. : 12/884925  
DATED : March 26, 2013  
INVENTOR(S) : Narendra Bhalchandra Ambhaikar et al.

Page 1 of 1

It is certified that error appears in the above-identified patent and that said Letters Patent is hereby corrected as shown below:

On the title page, item [73] should read:

(73) Assignee: Vertex Pharmaceuticals Incorporated, Cambridge, MA (US)

Signed and Sealed this  
Twenty-sixth Day of November, 2013

Margaret A. Focarino  
*Commissioner for Patents of the United States Patent and Trademark Office*